(12) United States Patent
Radziemski

(10) Patent No.: US 8,082,041 B1
(45) Date of Patent: Dec. 20, 2011

(54) BIO-IMPLANTABLE ULTRASOUND ENERGY CAPTURE AND STORAGE ASSEMBLY INCLUDING TRANSMITTER AND RECEIVER COOLING

(75) Inventor: Leon J. Radziemski, Tucson, AZ (US)

(73) Assignee: Piezo Energy Technologies, LLC, Tucson, AZ (US)

( * ) Notice: Subject to any disclaimer, the term of this patent is extended or adjusted under 35 U.S.C. 154(b) by 126 days.

(21) Appl. No.: 12/407,712

(22) Filed: Mar. 19, 2009

Related U.S. Application Data

(63) Continuation-in-part of application No. 12/136,743, filed on Jun. 10, 2008, now abandoned.

(60) Provisional application No. 60/944,325, filed on Jun. 15, 2007.

(51) Int. Cl.
*A61N 1/00* (2006.01)
(52) U.S. Cl. ............................................. 607/61; 607/33
(58) Field of Classification Search .................... 607/33, 607/61; 320/107, 137
See application file for complete search history.

(56) References Cited

U.S. PATENT DOCUMENTS

| | | | | |
|---|---|---|---|---|
| 4,748,985 A | * | 6/1988 | Nagasaki | 600/445 |
| 5,300,875 A | | 4/1994 | Tuttle | |
| 5,411,537 A | | 5/1995 | Munshi et al. | |
| 5,501,222 A | * | 3/1996 | Briggs | 600/453 |
| 5,545,942 A | * | 8/1996 | Jaster et al. | 310/341 |
| 5,555,887 A | * | 9/1996 | Fraser et al. | 600/472 |
| 5,560,362 A | * | 10/1996 | Sliwa et al. | 600/439 |
| 5,629,599 A | | 5/1997 | Malaspina et al. | |
| 5,703,474 A | | 12/1997 | Smalser | |
| 5,749,909 A | * | 5/1998 | Schroeppel et al. | 607/33 |
| 5,810,015 A | | 9/1998 | Flaherty | |
| 5,889,383 A | | 3/1999 | Teich | |
| 5,961,465 A | | 10/1999 | Kelly, Jr. et al. | 600/459 |
| 6,185,452 B1 | | 2/2001 | Schulman et al. | |
| 6,342,776 B1 | | 1/2002 | Taylor et al. | |
| 6,432,050 B1 | | 8/2002 | Porat et al. | |
| 6,475,170 B1 | | 11/2002 | Doron et al. | 600/587 |
| 6,654,638 B1 | * | 11/2003 | Sweeney | 607/9 |
| 6,720,709 B2 | | 4/2004 | Porat et al. | |
| 6,737,789 B2 | | 5/2004 | Radziemski et al. | |
| 6,764,446 B2 | | 7/2004 | Wolinsky et al. | 600/300 |
| 6,798,716 B1 | | 9/2004 | Charych | |
| 7,003,353 B1 | | 2/2006 | Parkhouse | |
| 7,024,248 B2 | | 4/2006 | Penner et al. | |
| 7,283,874 B2 | | 10/2007 | Penner | |
| 7,314,447 B2 | | 1/2008 | Park et al. | 600/459 |

(Continued)

FOREIGN PATENT DOCUMENTS

CA  2 364 853  9/2000

(Continued)

OTHER PUBLICATIONS

U.S. Official Action (mail) dated Jun. 25, 2009 (13 pgs).

*Primary Examiner* — Patrick Assouad
*Assistant Examiner* — Manuel Hernandez
(74) *Attorney, Agent, or Firm* — Hayes Soloway P.C.

(57) ABSTRACT

A bio-implantable energy capture and storage assembly, including an acoustic energy transmitter for contact with the skin, and an acoustic energy receiver—converter for converting acoustic energy to electrical energy; and a battery or capacitor connected to the energy converter. The acoustic energy receiver/converter is contained within a biocompatible implant.

33 Claims, 14 Drawing Sheets

U.S. PATENT DOCUMENTS

| | | |
|---|---|---|
| 7,489,967 B2 | 2/2009 | Von Arx et al. ............... 607/328 |
| 7,505,816 B2 | 3/2009 | Schmeling et al. .............. 607/61 |
| 2003/0137221 A1* | 7/2003 | Radziemski et al. .......... 310/339 |
| 2004/0002655 A1 | 1/2004 | Bolorforosh et al. ......... 600/459 |
| 2004/0172083 A1 | 9/2004 | Penner ............................ 607/35 |
| 2005/0033316 A1 | 2/2005 | Kertz |
| 2005/0075696 A1 | 4/2005 | Forsberg et al. |
| 2005/0187594 A1 | 8/2005 | Hatlestad |
| 2005/0256549 A1 | 11/2005 | Holzer |
| 2005/0288739 A1 | 12/2005 | Hassler, Jr. et al. |
| 2006/0009818 A1 | 1/2006 | Von Arx et al. |
| 2006/0136005 A1* | 6/2006 | Brisken et al. .................. 607/33 |
| 2006/0247738 A1 | 11/2006 | Schmeling et al. |
| 2007/0093875 A1 | 4/2007 | Chavan et al. |
| 2008/0021510 A1 | 1/2008 | Mi et al. .......................... 607/36 |
| 2008/0108915 A1 | 5/2008 | Penner ............................. 601/2 |
| 2008/0188755 A1 | 8/2008 | Hart ............................... 600/459 |
| 2008/0312720 A1 | 12/2008 | Tran et al. ....................... 607/61 |

FOREIGN PATENT DOCUMENTS

| | | |
|---|---|---|
| EP | 1 162 922 | 9/2000 |
| JP | 2000-350708 | 12/2000 |
| WO | WO 00/56241 | 9/2000 |
| WO | WO2006/119098 | 11/2006 |
| WO | WO 2008/156981 | 12/2008 |

\* cited by examiner

BIO-IMPLANTABLE ULTRASOUND ENERGY CAPTURE AND STORAGE ASSEMBLY INCLUDING TRANSMITTER AND RECEIVER COOLING

CROSS REFERENCE TO RELATED APPLICATION

This application is a continuation in-part of my prior U.S. application Ser. No. 12/136,743, filed Jun. 10, 2008 now abandoned, which application in turn claims priority from U.S. Provisional Application Ser. No. 60/944,325, filed Jun. 15, 2007.

STATEMENT REGARDING FEDERALLY SPONSORED RESEARCH OR DEVELOPMENT

This invention was made in part with Government support under grants number 1R43EB007421-01A1 and number R44EB007421 awarded by the National Institutes of Health (NIH). The Government has certain rights in the invention.

FIELD OF THE INVENTION

The invention is directed to bio-implantable energy capture and storage systems. The invention has particular utility as an energy capture and storage system designed to harvest acoustic energy transmitted through body tissues, and to convert that acoustic energy into electrical energy, and will be described in connection with each utility, although other utilities are contemplated.

BACKGROUND OF THE INVENTION

The lifetime of most implantable electro-devices is limited by the longevity of the power source. As the need for autonomous implanted sensors and devices increases, this will become even more critical. Future advances in power source design must continue to accommodate a range of battery functions in implants. In pacemakers, half the battery capacity is used for cardiostimulation and the other half to gather and telemeter information for monitoring purposes. Defibrillator and neurostimulator activities require burst mode applications of electrical shock that deplete the energy stored in the battery more quickly. Pacemakers and defibrillators are currently powered by primary batteries. Neurostimulators use primary or secondary batteries, the latter recharged by conversion of radio-frequency electromagnetic energy to electrical energy. Simpler and more effective recharging techniques are needed to power these types of devices.

Thus, a need exists for the development of power sources for implanted electro-medical devices. For example, when the battery of an implanted pacemaker has discharged to a predetermined threshold, surgery must be scheduled to replace the entire implant. Moreover, despite advances in battery technology, batteries currently consume 50% or more of the weight and volume of most implanted devices. Many new and emerging medical device technologies, such as enhanced inter-device telemetry, automated wireless alarm signaling, advanced sensors, and infusion pump therapies, continue to place demands on powering implanted systems .

The global market for implanted medical devices is significant and growing. Over 600,000 pacemakers were implanted worldwide in 2003, with 3 million of the devices in use at that time. In 2004, the overall market for cardiac rhythm management was estimated to be $8.9 billion, and by 2007 the total market for implantable and ingestible devices was predicted to exceed $24.4 billion. In addition to pacemakers and defibrillators, implantable devices now include pumps for diabetes and pain management, neurostimulators for pain therapy, and devices similar to pacemakers to electrically stimulate the stomach, throat, and other muscles.

Rechargeable batteries heretofore have not found wide use in implantable medical device applications. Patient compliance and recharge frequency limited the utility of rechargeable batteries. However, the increasing power needs for implanted devices directed at new therapies (defibrillators, drug pumps, left ventricular assist devices, and neurostimulators) combined with the development of advanced rechargeable lithium ion chemistries have awakened new interest in the use of rechargeable batteries in implants. A new recharging technology which is simple and user friendly, coupled with the improvements in rechargeable lithium ion or more advanced batteries, will prompt the medical community to rethink the issue of primary versus secondary batteries in conjunction with implantable medical devices.

The present method of recharging implantable batteries has been the radio frequency (RF) induction technique. Two coils, one outside the body and the second inside and connected to the device are placed in close proximity. A current generated in the outer primary coil induces a current in the inner secondary coil, and the voltage so generated is used to recharge the battery. While this technique can provide considerable power transmission, it has its disadvantages. The more power required, the larger the coils, leading to a heavy device with a large footprint both inside and outside of the body. Orientation of the two coils is critical, there is the potential for electromagnetic interference with other devices in the area, and nearby metal can be heated by eddy currents. Dielectric attenuation restricts usage to transmission through a few millimeters of skin. The ferrous metal parts inhibit magnetic-resonance imaging.

Several workers have proposed various implantable devices configured for transporting acoustic waves transmitted through the tissue of a patient to electrical current for powering the implanted device. See for example U.S. Pat. No. 7,283,874 to Penner. See also U.S. Pat. Nos. 5,749,909 to Schroeppel et al. and 6,185,452 to Schulman et al. Devices such as described above have, in practice, not proved to be satisfactory in that they were extremely limited in the amount of power that could be transmitted through the skin and tissue of the patient without causing excessive heating with the potential for tissue damage and the like, or because their objectives required lower power. This limitation of the prior art is, in part, a result of the use of PZT-based piezoelectric ceramic materials which are relatively inefficient when it comes to converting energy and transferring the energy through the skin and tissue.

SUMMARY OF THE INVENTION

The present invention overcomes the aforesaid and other deficiencies of the prior art, by providing an apparatus and method which generates acoustic energy, and transmits that acoustic energy wirelessly through skin and tissue to an implanted piezoelectric assembly comprising a piezoelectric element comprising lead-magnesium-niobate in lead-titanate (PMN-PT) that converts the acoustic energy into electrical energy. The technique is called ultrasound electrical recharging (USER). As will be discussed below, using piezo elements formed of PMN-PT provides unique advantages not seen with conventional piezo element formed of PZT. That electric energy can then be used to operate and/or charge or recharge a battery or capacitor to operate a pacemaker, defibrillator, neurostimulators, sensor readouts, or other implanted devices.

Although directed to implantable battery recharging, the USER method applies as well to any situation in which energy needs to be transmitted wirelessly through a barrier permeable by ultrasound, to power a device and/or to recharge a battery.

BRIEF DESCRIPTION OF THE DRAWINGS

This invention is described in preferred embodiments in the following description with reference to the Figures, in which like numbers represent the same or similar elements. and wherein.

DETAILED DESCRIPTION OF PREFERRED EMBODIMENTS

Figure 1A:
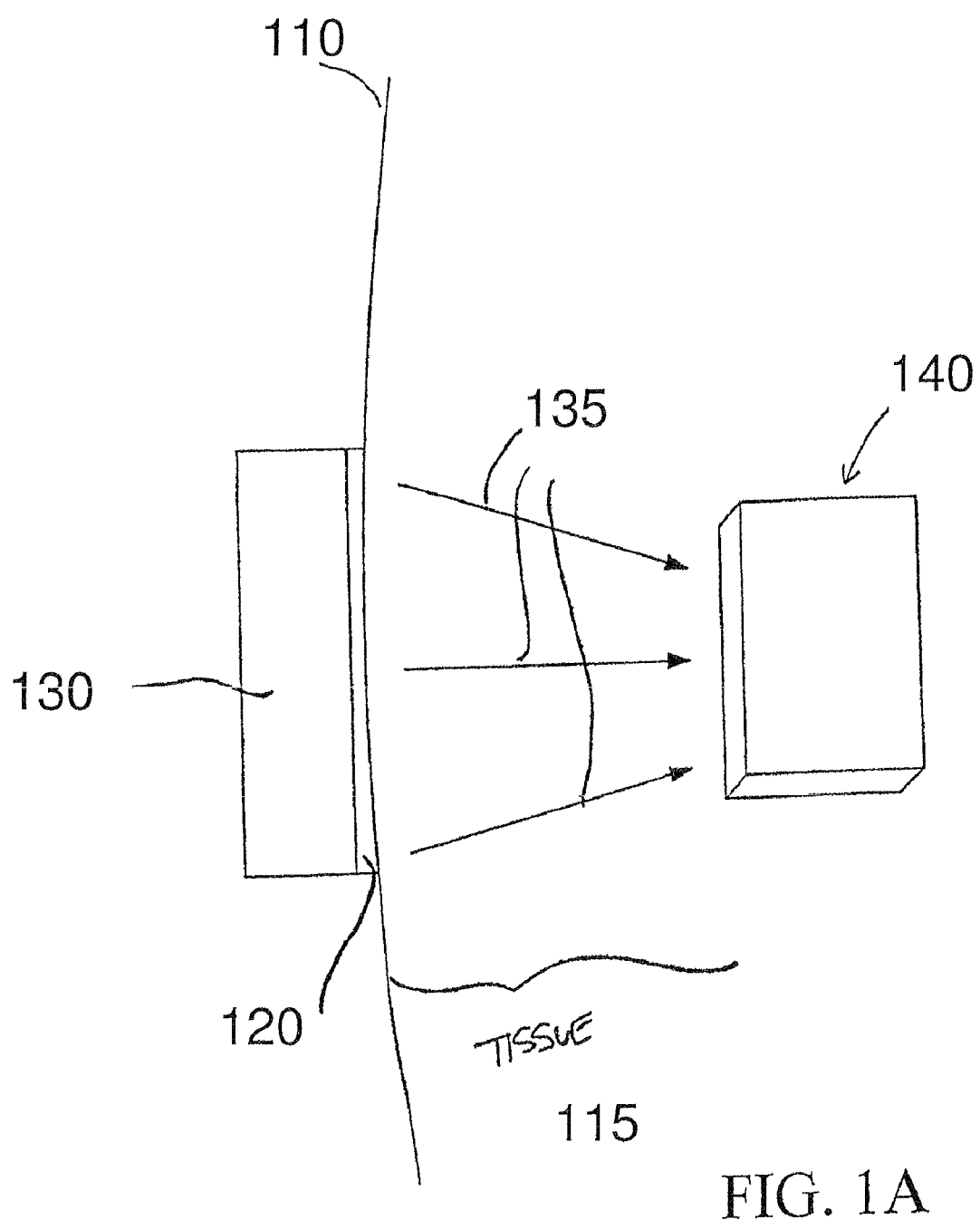
FIG. 1A schematically illustrates an apparatus made in accordance with the present invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. However, the invention may be practiced without one or more of the specific details, or with other methods, components, materials, and so forth. In other instances, well-known structures, materials, or operations are not shown or described in detail to avoid obscuring aspects of the invention.

The present invention utilizes acoustic energy waves to transmit energy into the body, where it is then converted to useful electrical energy. Those acoustic energy waves can be generated by any high frequency vibration source. By "high frequency," generally is meant a frequency of about 10 kHz and above, preferably operating at ultrasonic frequencies. i.e., above about 50 kHz, more preferably above about 100 kHz, even more preferably about 1 MHz to 10 MHz or more.

Unlike prior art systems such as discussed above, and which employed lead-zirconium-titanate ceramic piezoelectric elements, the present invention uses energy harvesting circuitry comprising piezoelectric elements comprising lead-magnesium-niobate in lead-titanate (PMN-PT), which because of better transduction coefficients, permits smaller transmitters and receivers, and less tissue heating due to smaller loss coefficients than for PZT. In a preferred embodiment of the invention, the piezoelectric assembly is formed using one or more PMN-PT crystalline piezoelectric materials, such as those recited in U.S. Pat. No. 6,737,789, which is hereby incorporated herein by reference. For purposes of this Application, the designation "PMN-PT" includes such crystalline piezoelectric materials. The relevant loss parameter, tan δ, is generally about 2-4 times smaller for PMN-PT than for PZT. Piezoelectric receivers can be embedded in devices, eliminating disadvantages of RF induction recharging, electromagnetic interference and RF-induced metal heating. Other electromechanical materials also can be used for ultrasound transducers useful in power transmission. These include: ceramic materials such as lead-zirconate-titanate (PZT), ceramic-filler composites, Micro Electro Mechanical Systems (MEMS), and Capacitive Machined Ultrasound transducers (CMUT) which are lead free.

Applicant's apparatus transmits acoustic energy wirelessly through a patient's skin and underlying tissue to an implanted receiver which converts the acoustic waves to electrical energy. If desired, the acoustic signal may also comprise a carrier for information transfer to and from the device. The implanted assembly uses an ultrasound energy receiver as a transducer that converts the incident acoustic waves into usable electrical power.

In the illustrated embodiment of FIG. 1A, an acoustic energy emitting device 130 is disposed on coupling medium 120 which in turn is disposed against skin surface 110. The coupling medium 120 may comprise carageenan, xanthum gum, alginic acid, silicon gel, or other acoustic impedance matching material that is suitable for long-term skin contact. At frequencies below 50 kHz, a coupling medium may not be necessary, because the acoustic impedance mismatch with air is much lower.

Acoustic wave emitting device 130 emits acoustic waves 135 which travel through tissue/organ 115. A portion of the acoustic waves emitted by device 130 are received by energy receiver/converter assembly 140. The depth below the skin of assembly 140 can vary from just below the skin to a depth of several inches, limited only by size and tissue absorption considerations. References herein to "transmitter" mean acoustic wave emitting device 130. Acoustic wave emitting device 130 preferably comprises one or more transducers, i.e., devices capable of operating at between a 0.1 percent and a 100 percent duty cycle, and that emits ultrasound vibrations that carry energy and power. By "ultrasound energy and power," Applicant means sound waves having a frequency of 10 kHz or greater, and a power level between about 0.1 watt and about 50 watts. The shape of the wave form may be a sine wave, or a square wave, or other wave from suitable to the application. It is known that there can be significant ultrasound power at harmonic frequencies. That power could add to the charging efficiency and/or provide other benefits for ultrasound recharging.

Figure 1B:
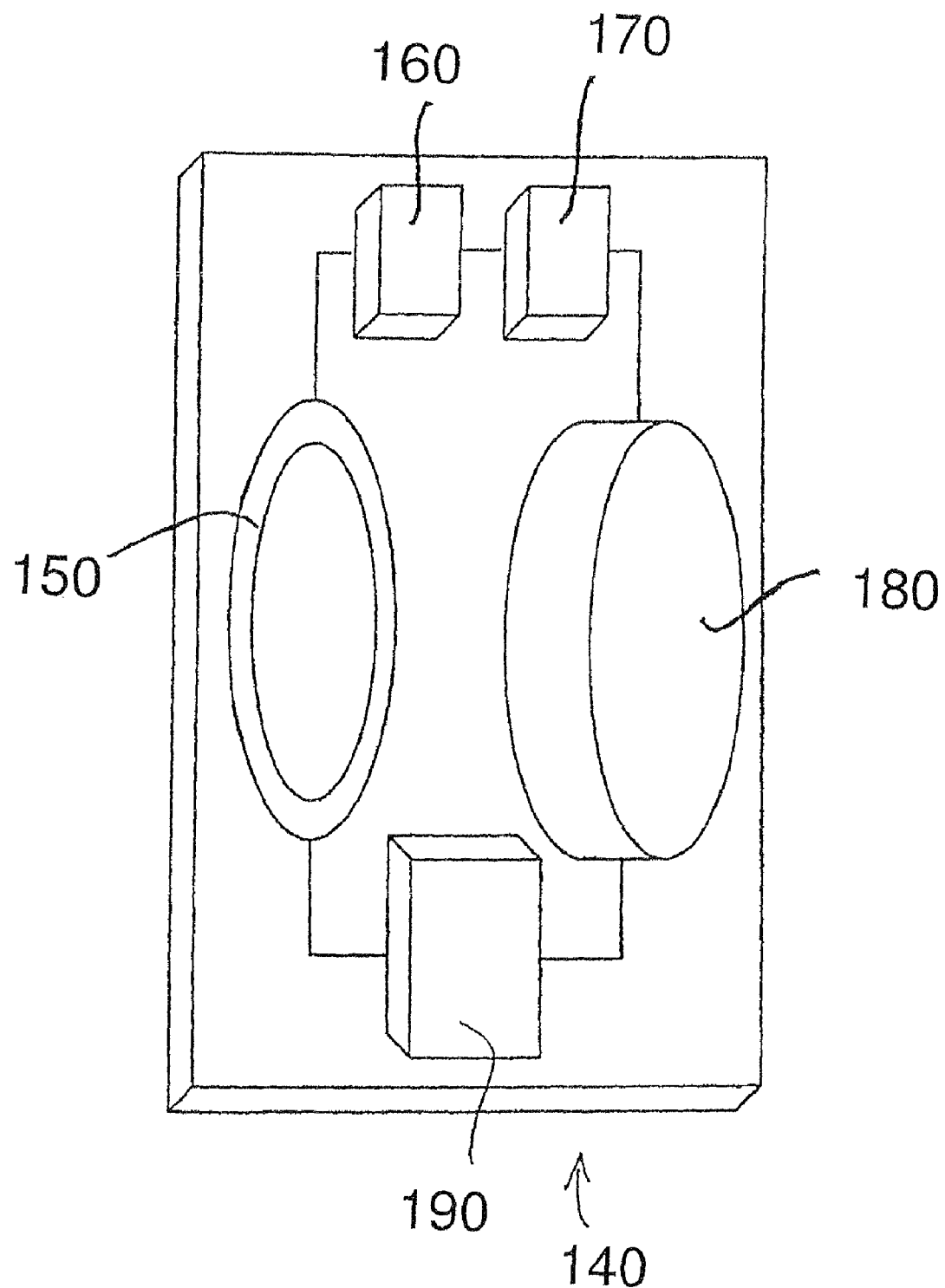
FIG. 1B schematically illustrates the implantable portion of the apparatus of FIG. 1.

Referring also to FIG. 1B, assembly 140 comprises an application package selected, for example, from the group consisting of a sensor, pump, USID tag, pacemaker, defibrillator, neurostimulator, or other implanted unit. In the illustrated embodiment of FIG. 1B, assembly 140 comprises receiver 150, memory device 160 which is in communication with receiver 150, application package 170 which is in communication with memory device 160, battery 180 which provides power to application package 170, and circuitry 190 which is in communication with receiver 150 and which provides recharging power to battery 180. Memory device 160 typically comprises electronic memory such as a PROM, EPROM, EEPROM, Flash PROM, compactflash, smartmedia, and the like. Also memory device 160 can communicate with external monitors via telemetry.

If desired, transmitter 130 and receiver 150 may have overlapping frequency resonances, or other advantageous combinations of frequencies. The size and mass of transmitter 130 and assembly 140 depend on power requirements. Typically, assembly 140 may comprise a volume of less than ten cubic centimeters and a mass less than 200 grams As will be discussed below, the piezo-electric element comprises a single-crystal piezoelectric such as PMN-PT which is 10 to 17 times more efficient than PZT in converting acoustic to electrical energy. This enhanced efficiency reduces both the required transmitter power and the receiver footprint, leading to more compact and lighter devices and reduced safety issues. A key advantage of single-crystal piezoelectrics, such as PMN-PT, is the sharp Q of their resonant frequency, and the gain in power transfer when they are used at that frequency. To maximize power transfer, it may be best to work at receiver's 150 resonant frequency.

Figure 2:
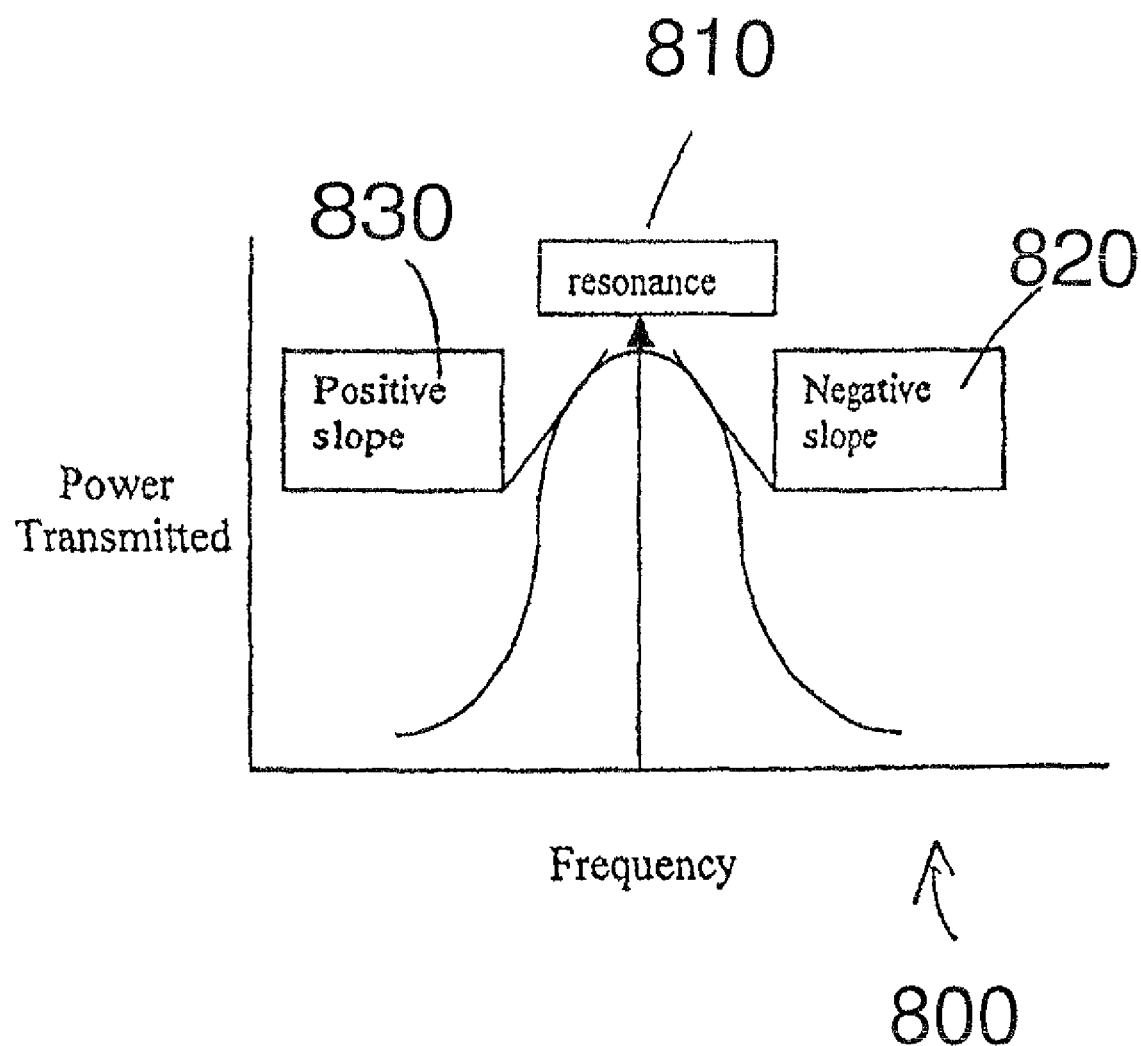
FIG. 2 shows power as a function of frequency in accordance with the present invention.

The transmitter-receiver system may tend to drift away from conditions for maximum power transfer for a variety of reasons, including temperature change in the receiver, and change in electrical characteristics such as impedance when power transfer is large. If one dithers the transmitter frequency around the resonant frequency of the receiver, the power as a function of frequency has a curve similar to a Gaussian. Preferably transmitter 130 comprises a servocontrol or feedback loop which can detect the decrease in the amplitude of the power transfer. In these embodiments, the feedback loop provides an adjustment signal to transmitter 130 which causes the transmitter to vary the frequency of the emitted acoustic waves to again reach resonance with receiver 150. The direction of the frequency correction is determined by electrically measuring the first and second derivatives of the change of the signal. Referring now to FIG. 2, with frequency increasing to the right and power towards the top, if a positive slope 830 is measured, then the frequency of the emitted acoustic waves is below the resonant frequency 810. Alternatively, if a negative slope 820 is measured, then the frequency of the emitted acoustic waves is above the resonant frequency 810.

Figure 3A:
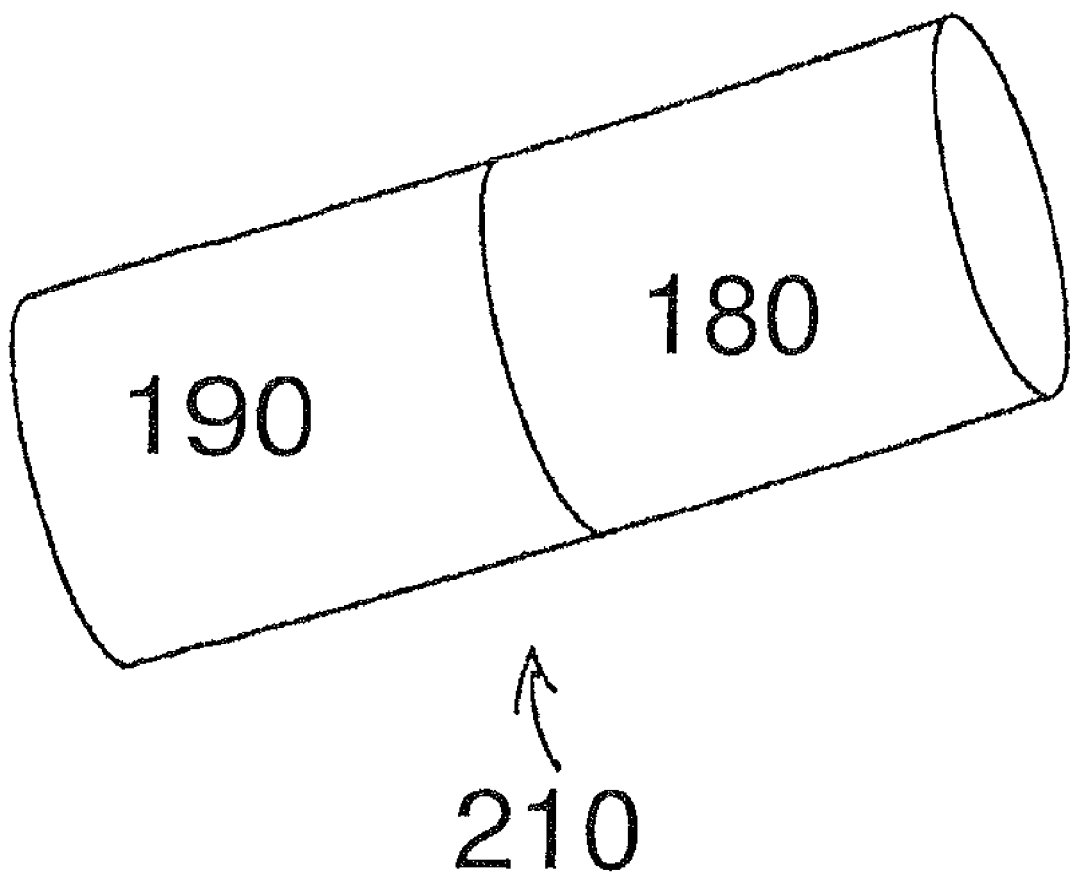
FIGS. 3A-3F illustrate various embodiments of circuitry, receiver and battery, as the case may be in accordance with various embodiments of the present invention.
Figure 3B:
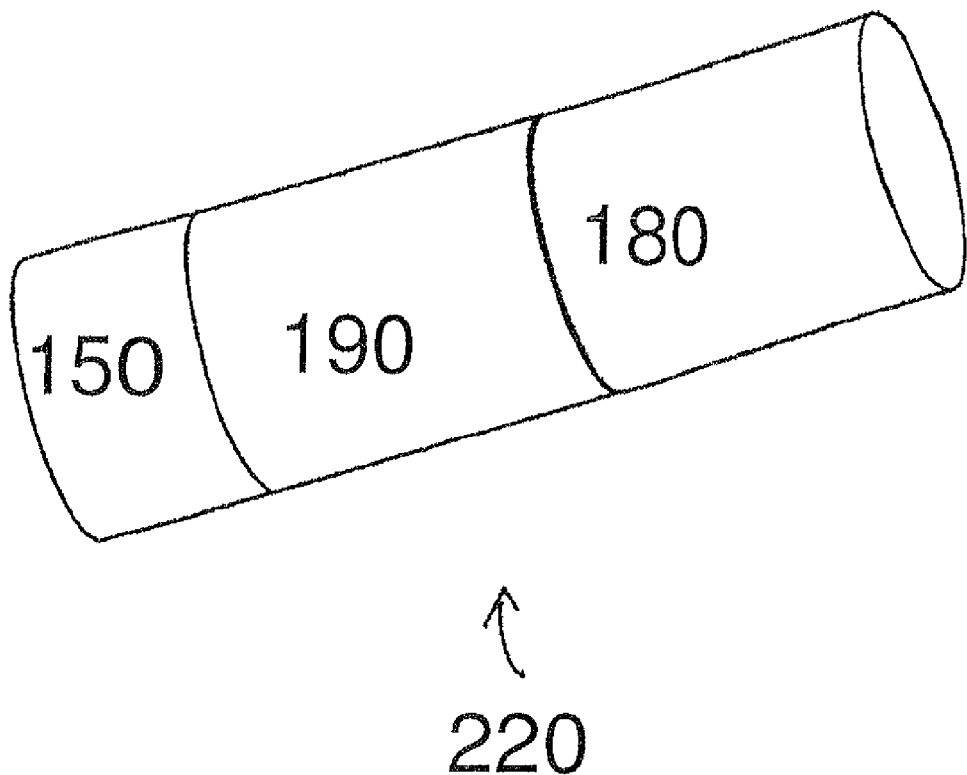
Figure 3C:
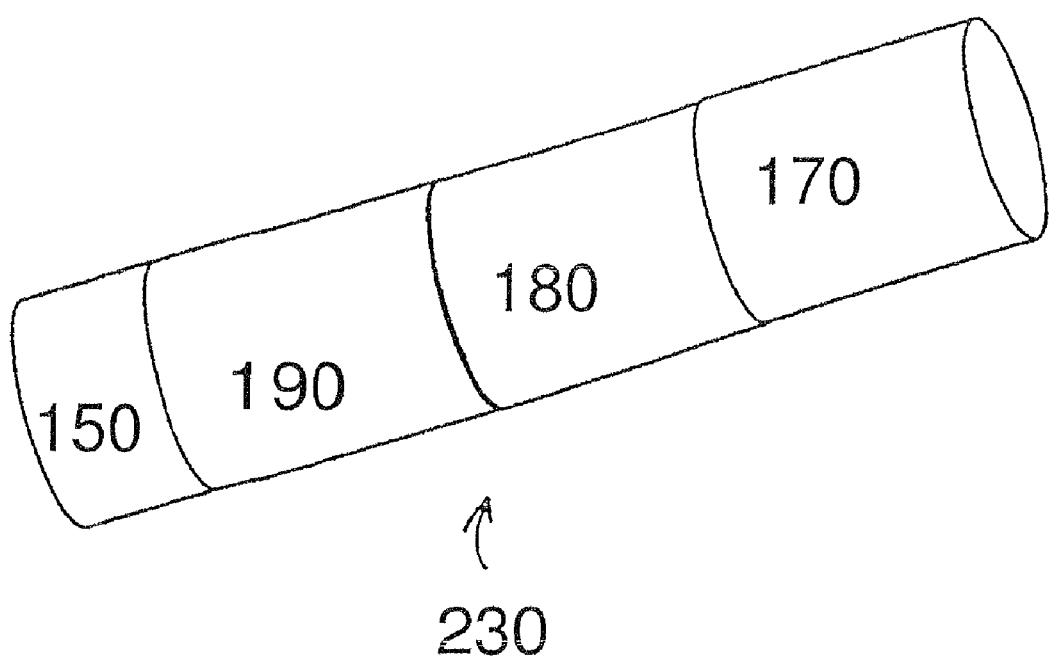
Figure 3D:
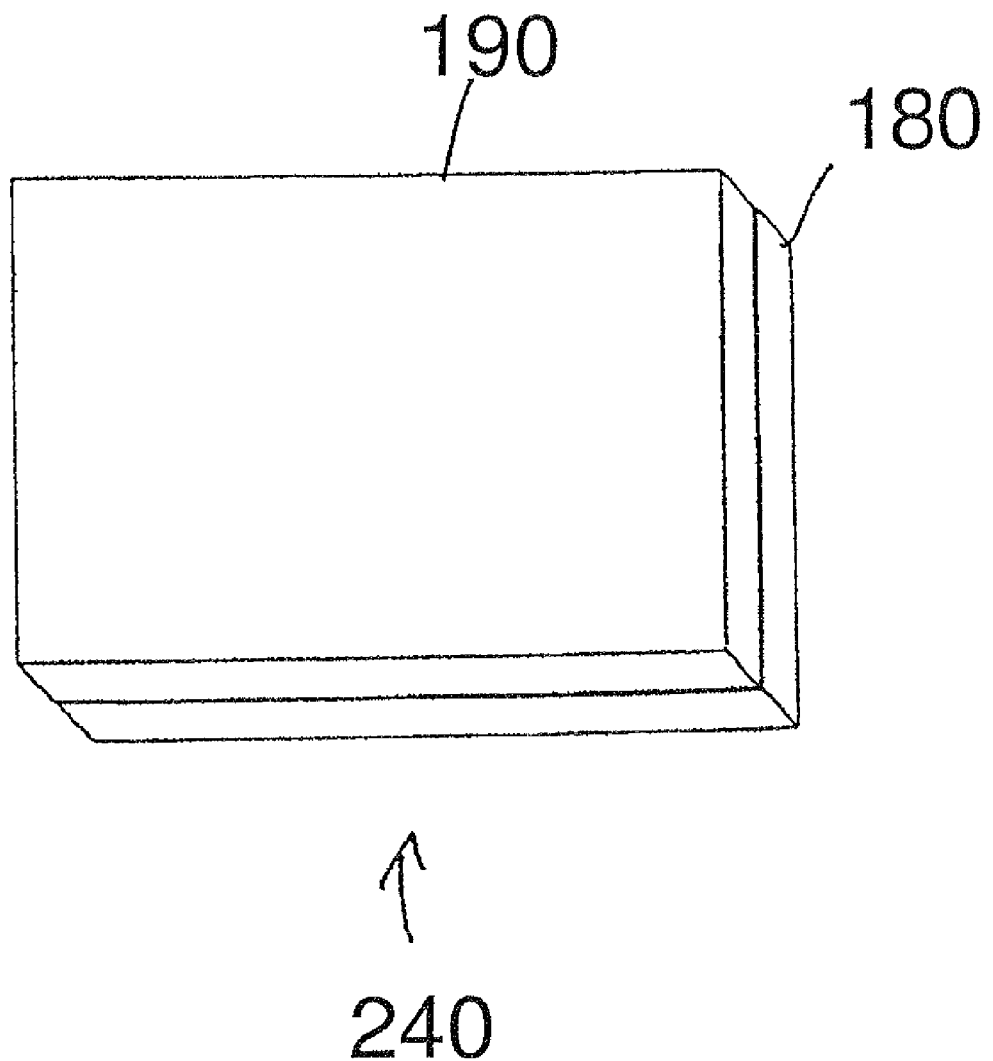
Figure 3E:
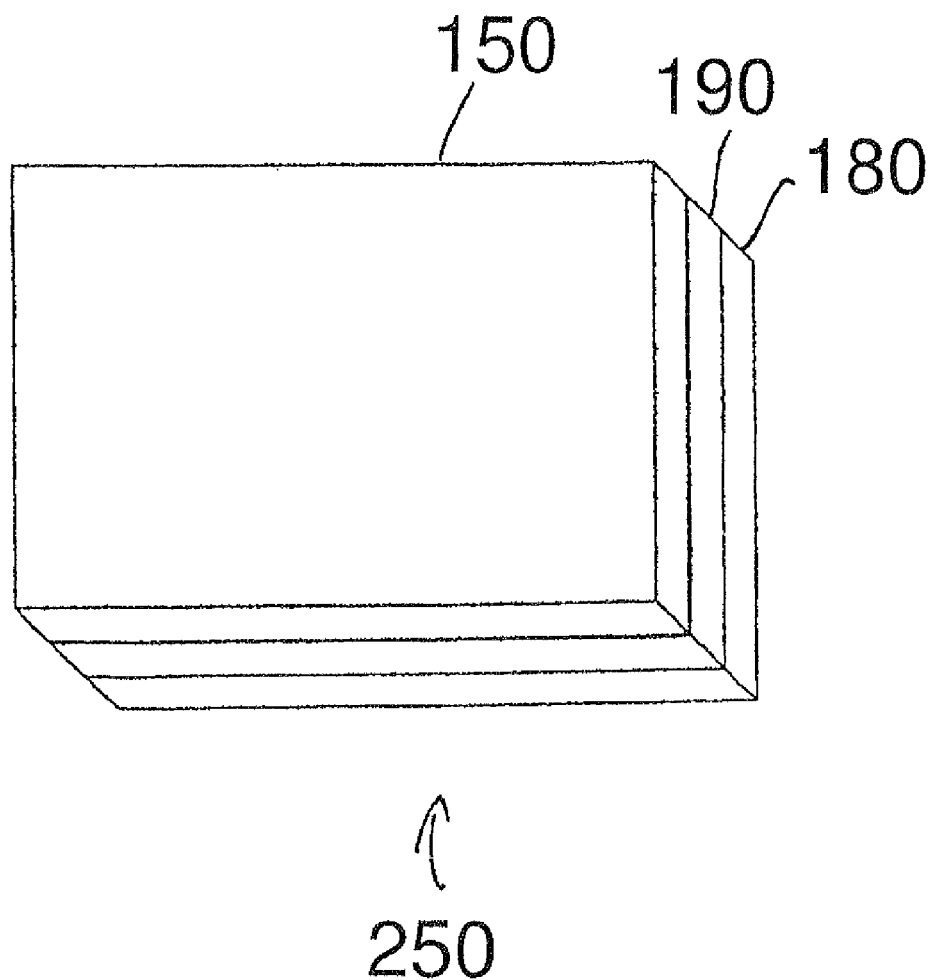
Figure 3F:
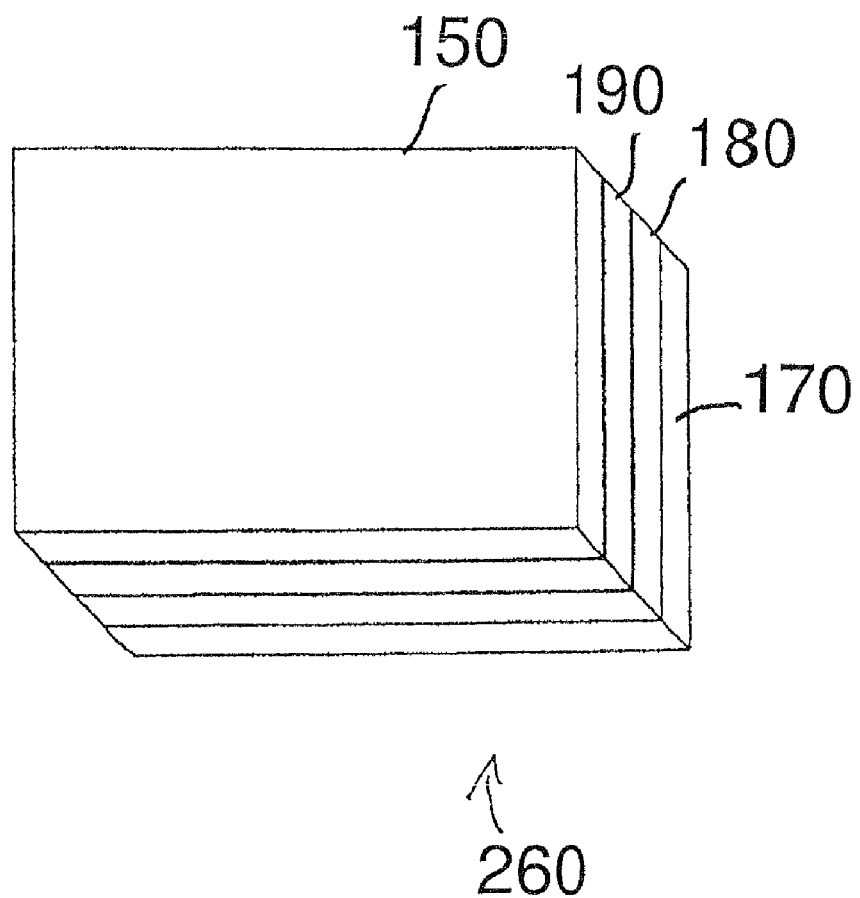

If desired, the receiver assembly may be collocated with the implanted device and sealed within a biocompatible material, presenting a unified form factor. Alternately, the receiver may be placed underneath but close to the skin at a depth of less than about one centimeter, with wires connected to a more deeply embedded application. Recharging protocols for battery 180 could be continuous or intermittent, as required by the drain on the battery. FIGS. 3A and 3D illustrate circuitry 190 and battery 180 formed as an integral device 210 or 240 which could be termed a piezo-battery, or a piezo-assisted battery, or an ultrasound energy recharging battery. FIGS. 3B and 3E illustrate receiver 150, circuitry 190 and battery 180 as an integral device 220 or 250. FIGS. 3C and 3F illustrate application package 170, receiver 150, circuitry 190 and battery 180 as an integral device 230 or 260. All of these devices can be described by the terms introduced above.

The primary material choice for generating and receiving ultrasound in the past several decades has been ceramic PZT because of its relatively low cost, easy workability, and moderate conversion coefficients. Recent research and development of new crystalline materials such as lead-magnesium-niobate dissolved in lead-titanate (PMN-PT), has resulted in a piezoelectric material with a force-to-charge conversion up to 10 times greater than PZT and 50 times larger than PVDF which materials are particularly well suited for use in bio-implantable devices as described in the instant application. Relevant parameters for PZT-5H, a common commercial piezoelectric material, and a PMT-33% PT composition are compared in TABLE 1. The units for d are Coulombs/Newton, and for g are Volt-Meter/Newton. The constant k is a dimensionless measure of efficiency.

TABLE 1

Comparison of properties of specific compositions of PZT and PMN-PT.

| Material | $d_{33}$ | $d_{31}$ | $g_{33}$ | $g_{31}$ | k |
|---|---|---|---|---|---|
| PZT-5H | $380 \times 10^{-12}$ | $260 \times 10^{-12}$ | $12.5 \times 10^{-3}$ | $8.0 \times 10^{-3}$ | ~0.57 |
| PMT-33%PT | $2820 \times 10^{-12}$ | $1330 \times 10^{-12}$ | $38.8 \times 10^{-3}$ | $-18.4 \times 10^{-3}$ | ~0.94 |

The symbols 33 and 31 refer to the direction of the force relative to the resultant electric field. Simply put, 33 describes the compression mode of the piezoelectric, 31 its bending mode. The power output of a piezoelectric is calculated for either compression or bending modes from $P=\sigma^2 gdVf$ where $\sigma$ is the stress, d and g are from TABLE 1 above, V is the volume of the material element, and f the frequency.

Thus, higher frequencies provide the capacity for higher power. For equal stress, volume and frequency, the gd product shows an advantage for PMN-PT of 23 for the 33 mode and 12 for the 31 mode, for an average of about 17. Since there are different compositions of both PZT and PMN-PT, the advantage will change slightly from material to material. However the PMN-PT advantage will remain. Hence the use of PMN-PT is preferred. It also appears that when using single crystals such as PMN-PT, it may be advisable to operate the transmitter and receiver at slightly different frequencies, aligned with minimum and maximum impedances in the frequency spectrum.

The ultrasonic frequencies 20 kHz to 1-3 MHz are of particular interest because of trade offs in safety issues. There is little tissue absorption in the lower range, but cavitation can be a problem. The latter danger eases at the higher range, but tissue absorption increases. Thus, Applicant's apparatus and method preferably operate at frequencies between 20 kHz and 1-3 MHz, but in certain cases frequencies up to 10 MHz may be advantageous.

Figure 7:
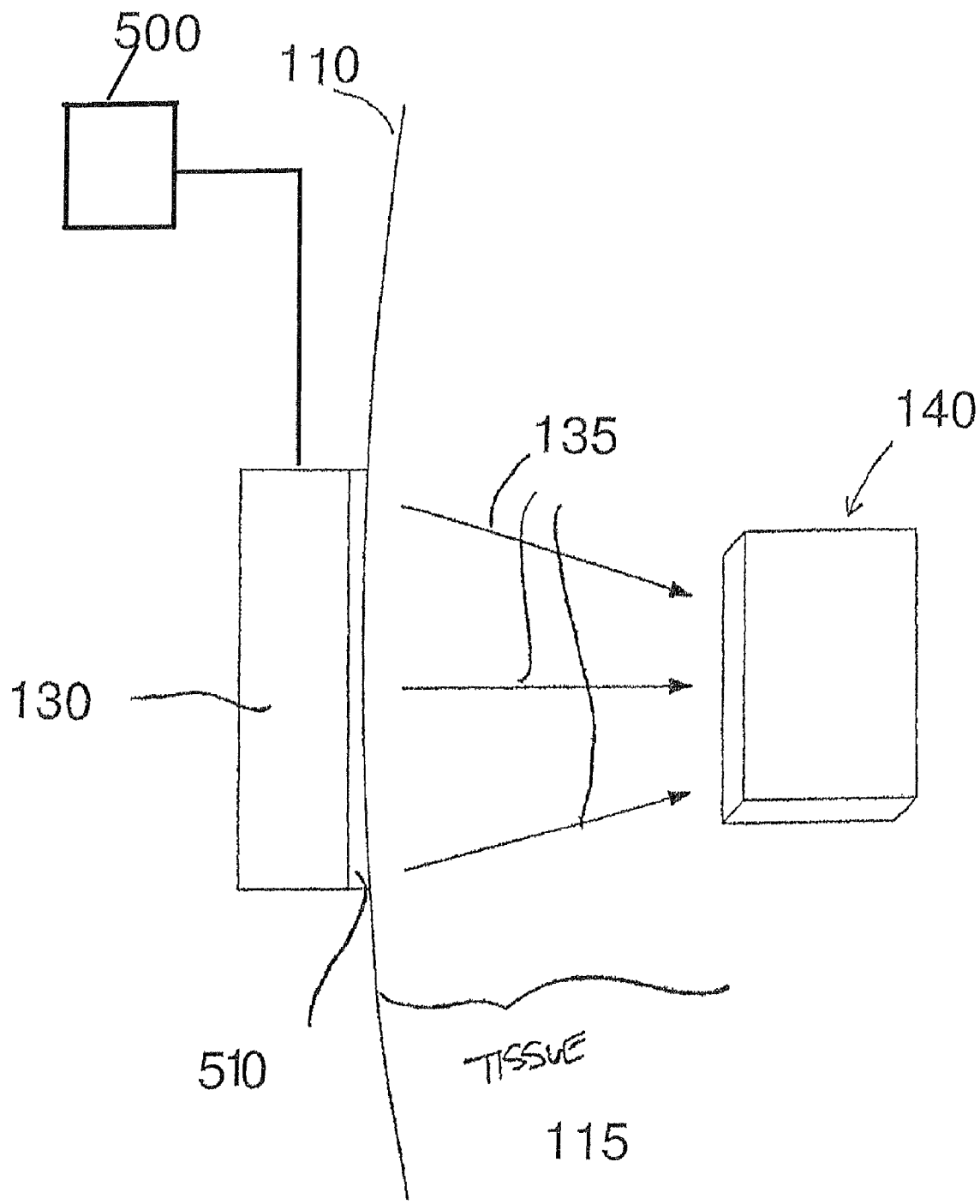
FIG. 7 schematically illustrates an apparatus made in accordance with the present invention.
Figure 8:
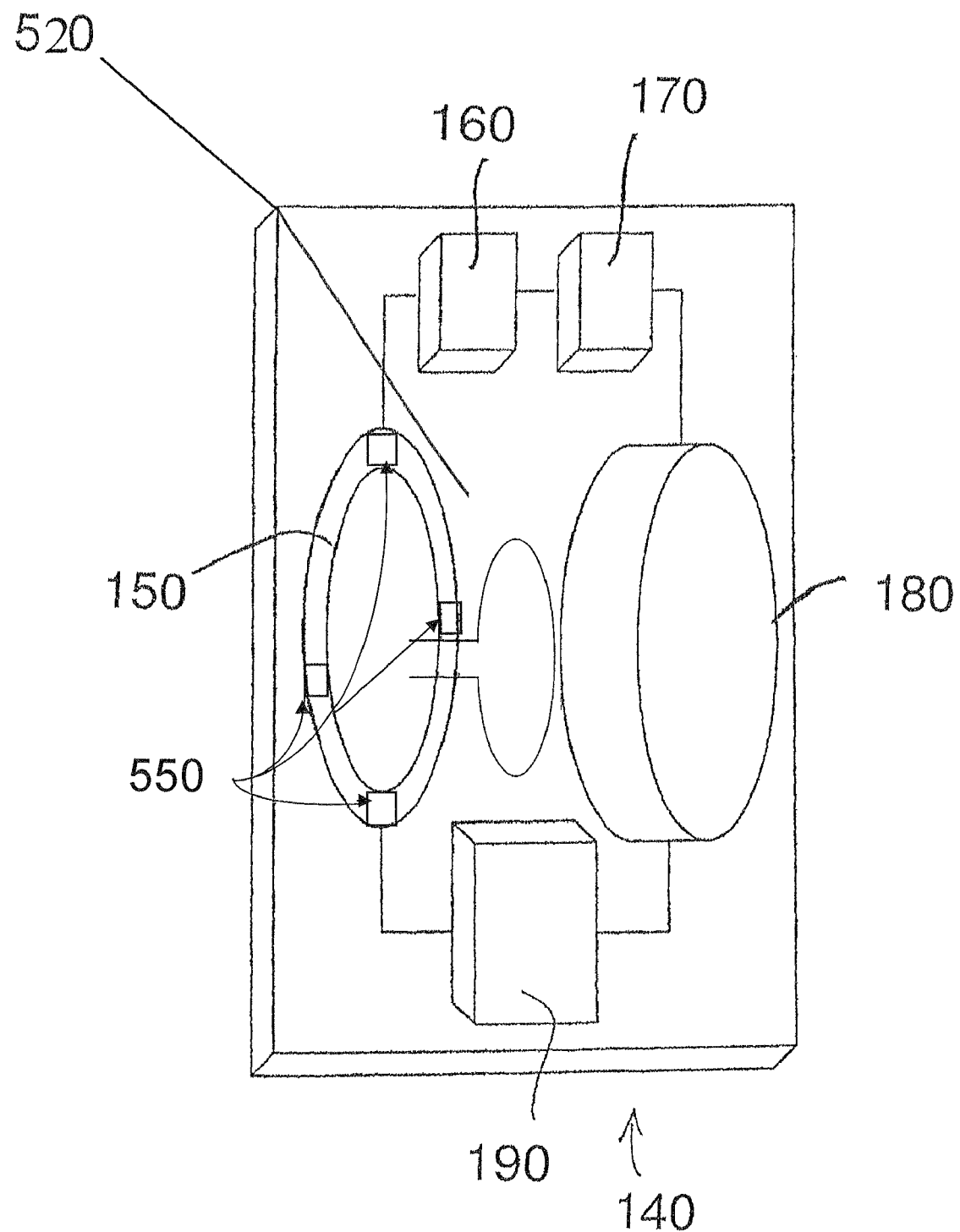
FIG. 8 schematically illustrates the implantable portion of the apparatus of FIG. 7.

Based on the small area of ultrasound imaging transmitter-receiver heads (typically less than 4 cm²), the present invention requires smaller footprints, and hence is lighter in weight than RF recharge heads delivering the same amount of power. One still needs to point the transmitter towards the receiver, but given the typical expansion of an ultrasound beam, misalignment will be less critical. However for maximum power transfer a system of alignment 500 (see FIG. 7.) would be advantageous. Four ultrasound sensors 550 (see FIG. 8) of diameter less than 2 millimeters, placed at the edge of each quadrant, 90 degrees apart, will sense the incoming acoustic wave. When the signal from the sensors is balanced, the alignment of transmitter and receiver is at an optimum. Alternately, image-guided systems, such as are now used for guiding biopsy needles could be employed, with a feedback loop, to center the transducers over one another. In these image-guided systems, an imaging ultrasound is used coincident with the transmitter. Angular misalignment can be overcome by using acoustic focusing elements in one or both of the transmitter and receiver. Also, if desired, the skin of the patient may be marked, e.g. with a permanent alignment indicia such as tattoo reference marks or the like. Also, pulse-echo ultrasound can be used to determine the location of the receiver. The location of the receiver also often times may be determined by palpating the area of the body where the receiver is believed implanted.

Figure 4:
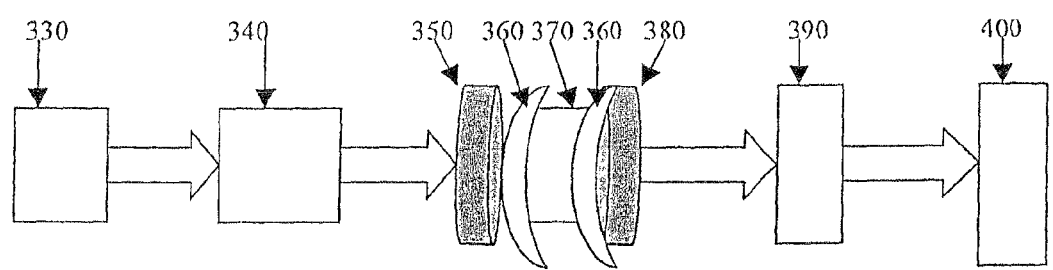
FIG. 4 schematic diagram of embodiment of the invention.

FIG. 4 shows a side-on schematic of the elements of a USER system. It consists of a frequency generating circuit 330, an amplifier 340, an ultrasound transmitter 350, a medium through which transmission occurs 360, material which provides acoustic impedance matching and excludes air from the transmission path 370, an ultrasound receiver 380, signal conditioning circuitry as needed 390, and systems to which the power is delivered 400. These systems include batteries, capacitors and loads of various impedances. PMN-PT may be used in both the ultrasound transmitter and receiver, or one unit may use PMN-PT and the other unit a different material, e.g. PZT. Applicant performed transmission using several matched ultrasound transducers, at 25, 40, 45, 92 kHz, 750 kHz, and 1.5 MHz. As noted in FIG. 4, a frequency source provided a voltage input to an amplifier that supplied power to the transmitter. The output signal from the receiver goes into a diode-rectifier bridge and then into a chip that controls battery storage, or a storage capacitor, or across a load.

The voltage to which a capacitor can be charged by this method is limited to the peak input voltage to the transmitter minus the losses in the diode bridge. To avoid the leveling effects of reaching this equilibrium Applicant evaluated the initial power input to the capacitor, where the voltage was far from equilibrium. This initial power was calculated from the rate of energy deposition into the capacitor, $d/dt$ ($\frac{1}{2} CV^2$). Applicant performed charging at different transmitter-receiver separations, different input voltages, different ultrasound transducers, and different skin simulants as the medium. Initial charging rates up to 500 mW were achieved. Also, rechargeable Li ion batteries from 35 mA-hr to 600 mA-hr capacities were charged at the rate of 0.5 to 1 C with the same medium and same apparatus.

Figure 5:
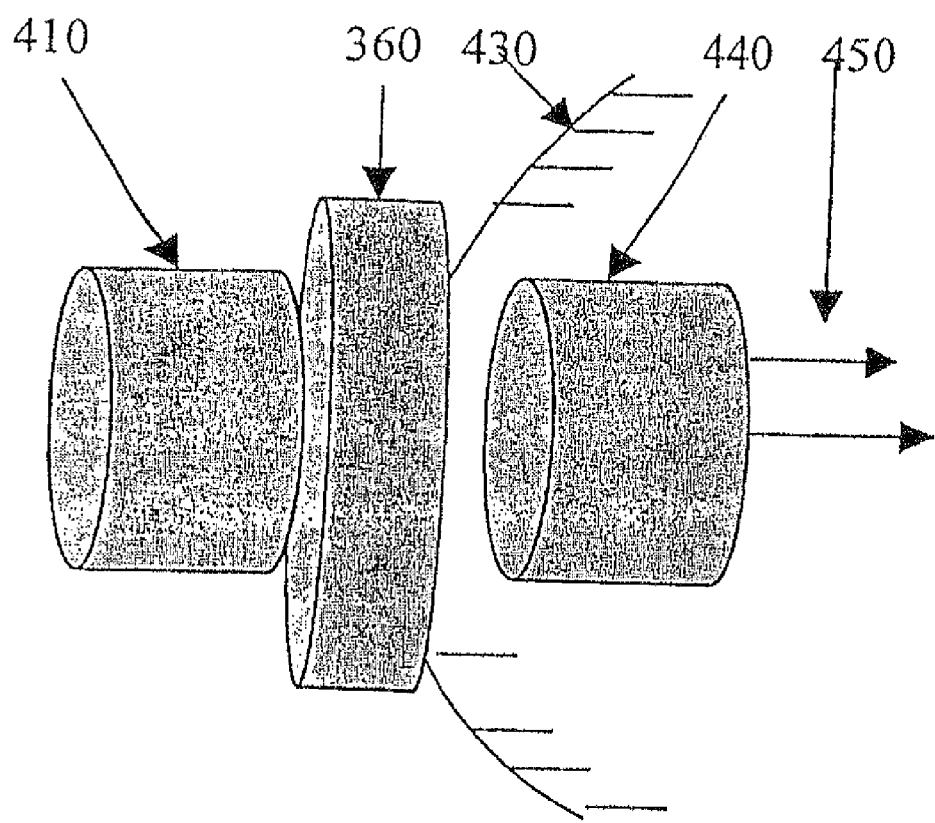
FIG. 5 Illustrates transmission through soft tissue.

FIG. 5 illustrates how transmission can practically be achieved through tissue. A canister 410 contains batteries or connection to an electrical outlet and items 330 through 350 in FIG. 4. Item 360 is the impedance matching, air-excluding medium, 430 is the skin and tissue through which the ultrasound is transmitted, 440 is the receiver 380 plus associated circuitry 390, and 450 represent leads, that when necessary connect to the heart or nerve ending, or other items to which a signal is to be applied. If the canister needs to be in place for a length of time, such as for overnight charging of a battery, then a strap or harness would secure the device to the patient. If canister 410 operates by rechargeable batteries, these batteries would be recharged from an electrical outlet in the periods between charging of the internal battery. As is well know, ultrasound can produce irreversible changes or damage in biological media by two major mechanisms, thermal and mechanical. The thermal mechanism is largely governed by the amplitude of the acoustic wave, the thermal absorption coefficient of the medium being considered, the length of time of the exposure, the cooling effect of the vasculature and thermal conductivity. Mechanically one can induce cavitation through hot spots. The length of time required for battery charging, i.e., the on-time of the sound beam and its time exposure periodicity, can be chosen such that the FDA guidelines of 0.72 W/cm² SPTA (spatial-peak, temporal average) are not generally exceeded. Another guideline is that the tissue temperature increase not exceed 2 degrees centigrade. Temperature increases are traditionally mitigated by slowing the charging rate. Such mitigation can also be accomplished by other methods. These will apply also to the present RF charging method and any other method that generates heat upon charging.

In one embodiment, a thermoelectric cooler is attached to the case of the ultrasound transmitter to cool the transmitter, skin, and tissue between the transmitter and receiver. The thermoelectric cooler may remove between 1 and 10 watts of thermal power, or a figure larger or smaller than that.

In another embodiment, a material 520 (see FIG. 8) with a phase change from the solid to the liquid state at a temperature no more than 2° C. above body temperature can be implanted adjacent to the ultrasound receiver to prevent the temperature of the receiver and nearby tissue from increasing more than 2° C. during the melting process. Pure, unadulterated lanolin is one such material, Certain other waxes also meet this criteria and advantageously may be used.

In another embodiment, a disposable liquid coolant package 510 (see FIG. 7) is placed between the transmitter and the skin to cool the transmitter, skin, and tissue between the transmitter and receiver. The liquid coolant package could be similar to the commercially available instant-cold pain relief packs, but with a cooling capacity designed to keep the skin and tissue temperature at a comfortable level.

The inclusion of a thermoelectric cooler or other type of cooling permits the use of piezo elements formed of materials other than PMN-PT, such as PZT.

A feature and advantage of the present invention is that the potential for changes or damage in biological media can be minimized.

Figure 6:
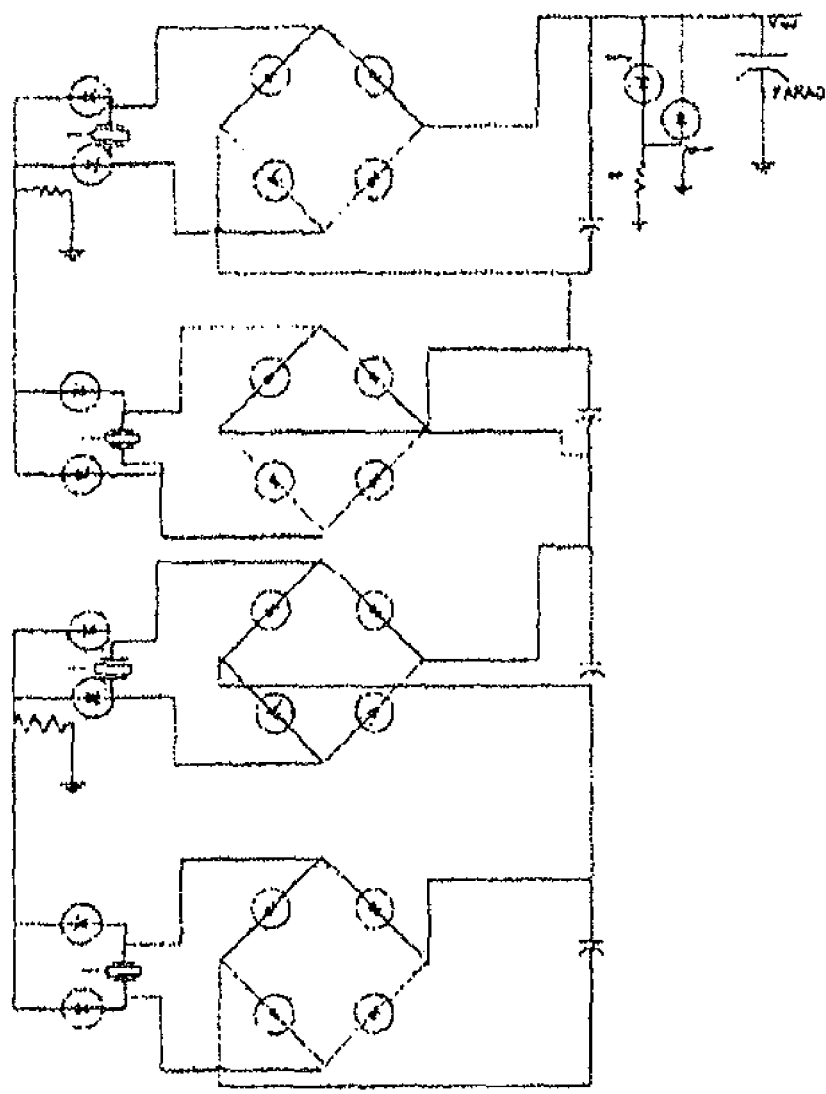
FIG. 6 illustrates a rectifier circuit that can be used to condition the power output of the ultrasound receiver.

In one embodiment, Applicant's apparatus and method couples the output electrical energy from a piezoelectric ultrasound transducer into a storage device. A full-wave rectifier circuit shown in FIG. 6 which derives from U.S. Pat. No. 6,737,789, the contents of which are incorporated herein by reference, has been used in the apparatus described hereinabove. The black arrows represent the diodes. In one preferred embodiment one can use multiple instead of single PMN-PT ultrasound receiver elements.

In another embodiment, Applicant's apparatus and method match the impedance of the piezo element ultrasound-receiver to the impedance of the battery-charging circuitry. This was done by adding reactive inductive and capacitive components on the output side of the receiver to provide reactive impedance with minimum power consumption.

The present invention offers several advantages over the prior art. Applicant's apparatus and method can improve human health by: (1) alleviating the distress, pain, and complications from battery replacement procedures, (2) increasing the functionality of the implant by providing more diagnostic output or burst mode power, and (3) reducing health care costs by minimizing the number of times that battery replacements have to be performed. Patients will benefit from better diagnostics and fewer surgeries for battery replacement. Physicians will benefit from increased capabilities for device interrogation and monitoring. Smaller lighter devices may assist in patient compliance issues. The invention also advantageously may be used, for example, to power micromuscles or other types of electrically powdered implanted devices. The energy capture and storage system of the present invention also advantageously may be used to power a variety of implants including; sensors, pumps, USID tags, pacemakers, defibrillators and neurostimulators which are given as non-limiting examples.

In another embodiment, the invention can also be used to transmit ultrasound energy and power wirelessly across other types of boundaries, not involved with transmission into the body. These could include the walls of transport containers, the walls of buildings, bulkheads or other types of boundaries in airplanes, trailers or ships, or any other boundary. Operational frequencies would vary depending on the length of the air path involved in the energy transmission. It is well known that sound and ultrasound are less attenuated at frequencies below 25 kHz.

In another embodiment, the invention can be used without the transmitter, in an environment where there are ultrasonic vibrations, such as near aircraft engines. In this case only the receiver-converter are required to provide the energy to a capacitor or battery. While the preferred embodiments of the present invention have been illustrated in detail, modifications and adaptations to those embodiments may be made without departing from the scope of the present invention.

I claim:

1. A bio-implantable energy capture and storage assembly, comprising:
   an acoustic energy transmitter configured to transmit acoustic energy at a power level rate between about 0.1 watt and about 50 watts;
   an acoustic energy receiver, said acoustic energy receiver also being an energy converter for converting acoustic energy to electrical energy;
   an energy storage device connected to said energy converter, wherein said acoustic energy receiver-converter is contained within a biocompatible implant configured to be implanted in a tissue, and said acoustic energy transmitter is separate from said implant; and
   a thermoelectric, disposable or reusable cooler in thermal contact with both the transmitter and the tissue, wherein said acoustic energy transmitter is contained in a case, and said cooler is disposed directly between the transmitter case and the tissue when in use.

2. The bio-implantable energy capture and storage assembly as claimed in claim 1, further comprising circuitry interconnecting said receiver and said energy storage device, wherein said circuitry provides recharging power to said energy storage device.

3. The bio-implantable energy capture and storage assembly as claimed in claim 2, further comprising a servocontrol or feedback loop that detects the amplitude of the charging current and adjusts the frequency of the transmitter toward the resonant frequency of the receiver.

4. The bio-implantable energy capture and storage assembly as claimed in claim 2, further comprising a servocontrol or feedback loop that detects the amplitude of the charging current and adjusts the alignment of the transmitter relative to the receiver to maximize power transfer.

5. The bio-implantable energy capture and storage assembly as claimed in claim 1, wherein said implant further comprises a sensor, a pump, a USID tag, a pacemaker, a defibrillator, micro-muscles or a neurostimulator.

6. The bio-implantable energy capture and storage assembly as claimed in claim 1, wherein the transmitter and receiver operate at the same frequencies.

7. The bio-implantable energy capture and storage assembly as claimed in claim 1, wherein the transmitter and receiver operate at different frequencies.

8. The bio-implantable energy capture and storage assembly as claimed in claim 1, wherein the acoustic energy transmitter is in contact with an impedance-matching material that is suitable for skin contact.

9. The bio-implantable energy capture and storage assembly as claimed in claim 1, further comprising an alignment system for aligning the transmitter over the receiver.

10. The bio-implantable energy capture and storage assembly as claimed in claim 9, wherein the alignment system comprises a pulse-echo ultrasound system.

11. The bio-implantable energy capture and storage assembly as claimed in claim 9, wherein the alignment system comprises an ultrasound imaging system.

12. The bio-implantable energy capture and storage assembly as claimed in claim 9, wherein the alignment system comprises four ultrasound sensors disposed on said acoustic energy receiver, and each of said sensors is equally spaced from its respective adjacent sensors.

13. The bio-implantable energy capture and storage assembly as claimed in claim 1, further including a phase change cooling material, implanted adjacent the receiver for cooling the receiver.

14. The bio-implantable energy capture and storage assembly as claimed in claim 13, wherein the phase change material comprises lanolin or a wax having a phase change temperature no greater than about 2° C. above body temperature.

15. The bio-implantable energy capture and storage assembly as claimed in claim 1, further comprising a servocontrol or feedback loop that detects the amplitude of the power transfer and adjusts the frequency of the transmitter toward the resonant frequency of the receiver.

16. The bio-implantable energy capture and storage assembly as claimed in claim 1, further comprising a servocontrol or feedback loop that detects the amplitude of the power transfer and adjusts the alignment of the transmitter relative to the receiver to maximize power transfer.

17. The bio-implantable energy capture and storage assembly as claimed in claim 1, wherein the frequency of the transmitter or the receiver is between about 20 kHz and 2 MHz.

18. A bio-implantable energy capture and storage assembly, comprising:
   an acoustic energy transmitter;
   an acoustic energy receiver, said acoustic energy receiver also being an energy converter for converting acoustic energy to electrical energy; and
   an energy storage device connected to said energy converter, wherein said acoustic energy receiver-converter is contained within a biocompatible implant, and said acoustic energy transmitter is separate from said implant, and
   a phase change cooling material implanted adjacent the receiver to cool the receiver, wherein the phase changing material changes phase from a solid state to a liquid state at a temperature greater than a normal temperature of the tissue, but no more than about 2° C. above the normal temperature of the tissue.

19. The bio-implantable energy capture and storage assembly as claimed in claim 18, wherein the phase change material comprises lanolin or a wax.

20. The bio-implantable energy capture and storage assembly as claimed in claim 18, further comprising circuitry interconnecting said receiver and said energy storage device, wherein said circuitry provides recharging power to said energy storage device.

21. The bio-implantable energy capture and storage assembly as claimed in claim 20, further comprising a servocontrol or feedback loop that detects the amplitude of the charging current and adjusts the frequency of the transmitter toward the resonant frequency of the receiver.

22. The bio-implantable energy capture and storage assembly as claimed in claim 20, further comprising a servocontrol or feedback loop that detects the amplitude of the charging current and adjusts the alignment of the transmitter relative to the receiver to maximize power transfer.

23. The bio-implantable energy capture and storage assembly as claimed in claim 18, wherein said implant further comprises a sensor, a pump, a USID tag, a pacemaker, a defibrillator, micro-muscles, or a neurostimulator.

24. The bio-implantable energy capture and storage assembly as claimed in claim 18, wherein the transmitter and receiver operate at the same frequencies.

25. The bio-implantable energy capture and storage assembly as claimed in claim 18, wherein the transmitter and receiver operate at different frequencies.

26. The bio-implantable energy capture and storage assembly as claimed in claim 18, wherein the acoustic energy transmitter is in contact with an impedance-matching material that is suitable for skin contact.

27. The bio-implantable energy capture and storage assembly as claimed in claim 18, further comprising an alignment system for aligning the transmitter over the receiver.

28. The bio-implantable energy capture and storage assembly as claimed in claim 27, wherein the alignment system comprises a pulse-echo ultrasound system.

29. The bio-implantable energy capture and storage assembly as claimed in claim 27, wherein the alignment system comprises an ultrasound imaging system.

30. The bio-implantable energy capture and storage assembly as claimed in claim 27, wherein the alignment system comprises four ultrasound sensors disposed on said acoustic energy receiver, and each of said sensors is equally spaced from its respective adjacent sensors.

31. The bio-implantable energy capture and storage assembly as claimed in claim 18, further comprising a servocontrol or feedback loop that detects the amplitude of the power transfer and adjusts the frequency of the transmitter toward the resonant frequency of the receiver.

32. The bio-implantable energy capture and storage assembly as claimed in claim 18, further comprising a servocontrol or feedback loop that detects the amplitude of the power transfer and adjusts the alignment of the transmitter relative to the receiver to maximize power transfer.

33. The bio-implantable energy capture and storage assembly as claimed in claim 18, wherein the frequency of the transmitter or the receiver is between about 20 kHz and 2 MHz.

\* \* \* \* \*

UNITED STATES PATENT AND TRADEMARK OFFICE
CERTIFICATE OF CORRECTION

| | | |
|---|---|---|
| PATENT NO. | : 8,082,041 B1 | Page 1 of 1 |
| APPLICATION NO. | : 12/407712 | |
| DATED | : December 20, 2011 | |
| INVENTOR(S) | : Leon J. Radziemski | |

It is certified that error appears in the above-identified patent and that said Letters Patent is hereby corrected as shown below:

Col. 1, line 18, the words "in part" should be deleted.

Signed and Sealed this
Twenty-fourth Day of July, 2012

David J. Kappos
*Director of the United States Patent and Trademark Office*